US010565850B2

(12) United States Patent
Schlichting et al.

(10) Patent No.: US 10,565,850 B2
(45) Date of Patent: Feb. 18, 2020

(54) CONTROL DEVICE FOR CONTROLLING AN ALARM OUTPUT AND METHOD FOR CONTROLLING AN ALARM OUTPUT AS WELL AS MEDICAL DEVICE

(71) Applicant: Drägerwerk AG & Co. KGaA, Lübeck (DE)

(72) Inventors: Stefan Schlichting, Lübeck (DE); Alexander Loose, Reinfeld (DE); Peter Haase, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 122 days.

(21) Appl. No.: 15/381,892

(22) Filed: Dec. 16, 2016

(65) Prior Publication Data

US 2017/0178488 A1 Jun. 22, 2017

(30) Foreign Application Priority Data

Dec. 17, 2015 (DE) .................. 10 2015 016 316

(51) Int. Cl.
*G08B 21/18* (2006.01)
*G08B 29/12* (2006.01)

(52) U.S. Cl.
CPC ........... *G08B 21/182* (2013.01); *G08B 29/12* (2013.01)

(58) Field of Classification Search
CPC ....... G08B 21/182; G08B 29/12; G06F 19/00; G06F 19/32; A61B 5/0015; A61B 5/6843
See application file for complete search history.

(56) References Cited

U.S. PATENT DOCUMENTS

| | | | |
|---|---|---|---|
| 2005/0146431 A1* | 7/2005 | Hastings ................ | A61B 5/002 340/539.12 |
| 2005/0271186 A1 | 12/2005 | Lichorowic et al. | |
| 2006/0049936 A1 | 3/2006 | Collins, Jr. et al. | |
| 2007/0229249 A1 | 10/2007 | McNeaal et al. | |
| 2013/0045685 A1* | 2/2013 | Kiani .................... | G08B 21/24 455/41.2 |
| 2015/0187202 A1 | 7/2015 | Janssen | |

FOREIGN PATENT DOCUMENTS

DE 103 40 396 A1 3/2005

* cited by examiner

*Primary Examiner* — James J Yang
(74) *Attorney, Agent, or Firm* — McGlew and Tuttle, P.C.

(57) ABSTRACT

A control device, controlling an alarm output, includes a data network interface, with a signaling interface for outputting a control signal indicating a request for an acoustic and/or optical alarm signal a memory unit and a processor. The data network interface is configured to receive a group message indicating a sender identity and a presence of an alarm state. The memory unit provides a first data set, which indicates a list with potential sender identities, as well as further a second data set, which indicates one or more alarm output time periods. The processor is configured to operate a timekeeping function, and to output the control signal via the signaling interface as a function of an agreement between the sender identity with one of potential sender identities, and as a function of a comparison of a current value of the timekeeping function with data of the second data set.

7 Claims, 11 Drawing Sheets

CONTROL DEVICE FOR CONTROLLING AN ALARM OUTPUT AND METHOD FOR CONTROLLING AN ALARM OUTPUT AS WELL AS MEDICAL DEVICE

CROSS REFERENCE TO RELATED APPLICATIONS

This application claims the benefit of priority under 35 U.S.C. § 119 of German Application 10 2015 016 316.7 filed Dec. 17, 2015, the entire contents of which are incorporated herein by reference.

FIELD OF THE INVENTION

The present invention pertains to a method for controlling an alarm output and a control device for controlling the output of an alarm, with a data network interface and with a signaling interface for outputting a control signal. The present invention further pertains to a medical device for analyzing physiological patient data or for monitoring an operating state of at least one device having an alarm signal output unit and an input unit.

BACKGROUND OF THE INVENTION

A scenario is known in which a medical device monitors physiological patient data and controls an output of an alarm signal by means of a comparison of the physiological patient data with reference values. The alarm signal may be outputted here by the medical device itself, or else a request message for requesting the output of an alarm signal may be sent by the medical device to another device. As an alternative for monitoring physiological patient data, status data can be monitored, which indicate an operating state of other technical devices or partial devices on or in the medical device; for example, the falling off of an electrode or an increase in the pressure in a tube can be detected and indicated. An alarm signal can likewise be detected by comparing the status data with corresponding reference values.

US 2005/0271186 A1 discloses a system in which a central unit is used to determine, by a configuration of a user, which telephone shall be reached by means of a network at which times and in case of which occurring events, so that the telephone will then output an output of a signal or an alarm signal. US 2007/0229249 A1 shows a system in which an alarm is outputted in a coordinated manner by an alarm messenger, in which alarm signals are sent to different receiving units based on data of a data bank. Thus, a concept, in which a central unit is configured to subsequently send different alarm signals to different output units at different times, is proposed in both prior-art documents.

SUMMARY OF THE INVENTION

An object of the present invention is to execute the output of alarm signals in a clinical setting by means of a plurality of devices in a coordinated manner and to make the output of alarm signals preferably possible in the process to minimize alarm signals to be outputted to the different devices while an alarming function is, in principle, ensured at the same time.

The present invention pertains to a control device for controlling the output of an alarm, having a data network interface, a signaling interface for outputting a control signal, which indicates the request for the output of an acoustic and/or optical alarm signal, at least one memory unit, at least one processor, as well as an alarm output unit for outputting an optical and/or acoustic warning, which is configured to operate a timekeeping function, the data network interface being configured to receive a group message, which indicates the sender identity of a sender of the group message and which further indicates the presence of an alarm state, wherein the memory unit provides a first data set, which indicates a list with potential sender identities, and further a second data set, which indicates one or more time periods, during which an alarm signal shall be outputted, wherein the processor is further configured to output the control signal via the signaling interface as a function of an agreement between the sender identity indicated in the group message with one of the potential sender identities as well as further as a function of a comparison of a current value of the timekeeping function with data of the second data set.

The control device has an input interface for receiving an input signal, which indicates the acknowledgment of the alarm signal by a user, wherein the processor is further configured to suppress the output of the control signal in the presence of the input signal and further to send a status message, which indicates the acknowledgment of the alarm signal by the user, to the sender of the group message via the data network interface. The present invention is advantageous because it is possible hereby to completely or at least temporarily suppress the output of the control signal after acknowledgment of the alarm signal on an input unit by the user in order to not needlessly task the acoustic and/or optical attention of the clinical staff any longer. Further, by sending the status message, the sender of the group message is informed that a user has acknowledged the alarm by an input on the control device.

The control device has an alarm signal output unit itself, which outputs an optical and/or acoustic alarm signal as a function of the control signal. The control signal is preferably sent as a data signal by the control device to another device, and this additional device will then, in turn, be able to perform the output of an optical and/or acoustic alarm signal, depending on the control signal, via its own alarm signal output unit. The second data set indicates respective time periods with a respective beginning and a respective end of the time period. The control device suppresses the output of the control signal preferably no later than when this is indicated by the time periods of the second data set.

The group message in the sense of this application is a data network message. Such a group message as a data network message is sent to one or more network units of a group of network units. The group of network units is then preferably defined by group identification data, e.g., a multicast address or a set of a plurality of respective data network addresses of respective network units. A group message in the sense of this application is consequently a data network message of the type of a broadcast message, an anycast message, a multicast message or one or more unicast messages.

The group message may be sent, for example, by a patient monitor or a medical device for analyzing physiological patient data or for analyzing operating states within a data network, in order to inform the control device according to the present invention that the output of an alarm shall be performed or actuated by the control device. The output of the alarm may be executed on the control device itself or preferably on a device that is in communication connection with it and hence it does not consequently have to be performed on the medical device itself, which is located directly at the hospital bed. Thus, the patient is not needlessly disturbed or bothered by the alarm. The control device may be here, for example, a so-called pager for a clinician, a smartphone of a physician or else an alarm unit in a room for nursing staff.

The control device according to the present invention for controlling the output of an alarm is advantageous because the output of the control signal does not generally take place as a request for outputting an acoustic and/or optical alarm signal in case of indication or the presence of the alarm state, but also as a function of the time periods indicated in the second data set. Therefore, an actual alarming is only performed when there currently is a time period at which the control device shall, indeed, perform the outputting of an alarm; this takes place by a comparison of the current value of the timekeeping function with the time periods indicated in the second data set. The control device can thus be configured by the second data set in a simple manner in order for the control device not to generate or actuate the outputting of the alarm signal by the control signal for all times or time periods. As a result, the control device can be assigned by, e.g., the second data set to a class of alarming devices because, e.g., different control devices may provide respective different second data sets for indicating respective different time periods of a particular alarming activity. If the output of the control signal is preferably suppressed at the latest when this is indicated by the time periods of the second data set, it is achieved as a result that a first control device of a first alarm class or device group suppresses the output of the alarm signal also when a user made no input on the control device. The output of an alarm can now take place automatically on another control device of another alarm class or device group, and the total number of alarm signals sent is reduced by suppressing the output of an alarm on the first control device.

The group message preferably further indicates a type of an alarm state by means of a data element, the second data set further indicating an assignment of the time periods to types of alarm states, and the processor being configured to take into account the type of the alarm state, which type is indicated in the group message, in the course of the comparison. This configuration of the present invention is advantageous because the output of the alarm can be controlled as a function of an alarm type, so that different time periods of outputting the alarm signal can be provided for different types of alarms.

The processor is preferably further configured to check, based on a status information, whether the control signal can reach an alarm signal output unit or not, and further to send a status message, which indicates the successful actuation of the alarm signal output unit, to the sender of the group message via the data network interface in case of a positive result of the checking and in case the control signal starts being outputted. This configuration of the present invention is advantageous because the control device can check, based on the status information, whether the output of an alarm via an alarm signal output unit is possible in the first place and further it can send a status message to the sender of the group message in case of a positive result of the checking, said status message informing the sender that an alarm signal is outputted to an alarm signal output unit.

The data network interface is preferably further configured to receive a status message, which indicates whether another control device is currently successfully actuating an alarm signal output unit assigned to it, the processor being further configured to output the control signal via the signaling interface as a function of the presence of the status message. This configuration of the present invention is advantageous, because it is made possible hereby that different control devices of different alarm classes can be provided, which can perform a respective, own alarm output at different time periods, but, further, a control device does not perform the outputting of the control signal for requesting the output of an alarm signal if the alarm is already outputted on another control device; this is indicated by the status message. It is made possible hereby that, e.g., two different control devices of different alarm classes can have common, overlapping time periods for alarming, but the two control devices do not cause alarming simultaneously in case of overlapping time periods, but only one of these two control devices will cause or actuate an alarming, while the other control device suppresses its output of an alarm or alarm actuation during the overlapping time period. It is made possible hereby that the actual number of control devices of different alarm classes, which indeed actuate the output of an alarm for common, overlapping time periods, is minimized, it is ensured at the same time that at least one control device of one alarm class will actuate the output of an alarm during this overlapping time period.

The data network interface is preferably configured, furthermore, to receive a status message, which indicates that another control device has detected an acknowledgment of an alarm signal by a user, the processor being further configured to suppress the output of the control signal in the presence of the status message. This configuration of the present invention is advantageous, because the control device can trust that a user has already acknowledged at another control device an alarm signal outputted there, so that the number of acoustic and/or optical alarm signals can be minimized by suppressing the output of the control signal on the control device. The data network interface is preferably a data network interface to a first data network, the signaling interface being further a second data network interface to a second data network, and the control signal being a data signal. This configuration of the present invention is advantageous because the control device can assume a so-called gateway functionality, in which the control signal can be sent in the form of a data signal to another unit or to another network participant, preferably a pager, through the second data network. The alarm output unit for outputting the alarm signal or alarm signals can then be provided at this additional unit or at this additional network participant of the second data network. It is made possible hereby to coordinate the outputting of the alarms, as was described above, even if the control device itself does not have an alarm signal output unit for outputting the alarm signal, but if the alarm signal output unit is provided at the additional unit or the additional network participant.

The memory unit preferably further provides a third data set, which indicates a list of network participants of the second data network. This configuration of the present invention is advantageous because the control device can now access the provided list of the network participants of the second data network in order to decide to which network participant of the second data network it will send the control signal in the form of a data signal.

Further, a method for controlling the output of an alarm is proposed, which comprises the receipt of a group message, which indicates the sender identity of a sender of the group message and further the presence of an alarm state; the provision of a data set, which indicates a list with potential sender identities, and further of a second data set, which indicates time periods, during which an alarm signal shall be sent; the operation of a timekeeping function; the output of a control signal, which indicates a request for an acoustic and/or optical alarm signal, as a function of an agreement between the sender identity indicated in the group message and one of the potential sender identities and further as a function of a comparison of a current value of the timekeeping function with data of the second data set. The second data set indicates respective time periods with a respective beginning and with a respective end of the time period. The output of the control signal is preferably suppressed no later than when this is indicated by the time periods of the second data set.

Further, it is proposed that the method according to the present invention be executed with computer program means on at least one processor.

Further, a program with a program code for executing the method according to the present invention is proposed, if the program code is executed on a computer, a processor or a programmable hardware component.

Further, a processor is provided for a control device for controlling the output of an alarm, wherein the processor is configured to receive a group message, which indicates a sender identity of a sender of the group message, and further the presence of an alarm state; further, to receive a data set, which indicates a list with potential sender identities, as well as further a second data set, which indicates time periods, during which an alarm signal shall be outputted, as well as further to operate a timekeeping function, and further to output a control signal, which indicates a request for outputting an acoustic and/or optical alarm signal, as a function of an agreement of the sender identity indicated in the group message with one of the potential sender identities and as a function of a comparison of a current value of the timekeeping function with data of the second data set. The second data set indicates respective time periods with a respective beginning and with a respective end of the time period. The processor suppresses the output of the control signal preferably no later than when this is indicated by the time periods of the second data set.

Advantages of the control device provided likewise apply to the method provided. Likewise, these advantages apply to the processor provided.

Further, a medical device for analyzing physiological patient data or for monitoring a technical device is proposed, comprising an alarm signal output unit; an input unit for manual actuation by a user; at least one interface for receiving at least one signal, which indicates physiological measured values of a patient or at least an operating state of a device; at least one memory unit for providing a first data set, which indicates reference values, and for providing a second data set, which indicates a time period, after the end of which an alarm shall, in principle, be outputted to the alarm signal output unit; at least one data network interface; at least one processor, wherein the processor is configured to detect the presence of an alarm state by a comparison of the physiological measured values or the operating state with the reference value, and to output a group message, which indicates the presence of an alarm state, if the alarm state is detected via the data network interface, and is further configured to provide a timekeeping function, the processor being further configured to receive, via the data network interface, a status message, which indicates an acknowledgment of the alarm state by the user input, and to perform the outputting of an alarm signal via the alarm signal output unit after sending the group message as a function of a current value of the timekeeping function, of the second data set, which indicates the time period, of the presence of the status message and of the presence of an input on the input unit.

The operating state is preferably an operating state of a partial device at or in the medical device. For example, the medical device is a so-called patient monitor, and the signal indicates which operating state is currently given for an ECG electrode connected to the patient monitor, e.g., whether the ECG electrode is positioned on a human body or whether the electrode is not (no longer) positioned on a human body. For example, the medical device is an infusion pump device, which checks a pressure in the corresponding tube system by means of a manometer and derives an operating state herefrom.

The operating state is preferably an operating state of another device, which differs from the medical device. The signal indicates in this case an operating state of an infusion pump device separate from the patient monitor, e.g., on a patient monitor.

The present invention will be explained in more detail below on the basis of special embodiments without limitation of the general inventive idea on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 9b is a view showing a diagram of time periods in connection with the method steps from FIG. 9a;

FIG. 10b is a view showing a diagram of corresponding time periods in connection with the method steps from FIG. 10a;

DESCRIPTION OF THE PREFERRED EMBODIMENTS

Figure 1:
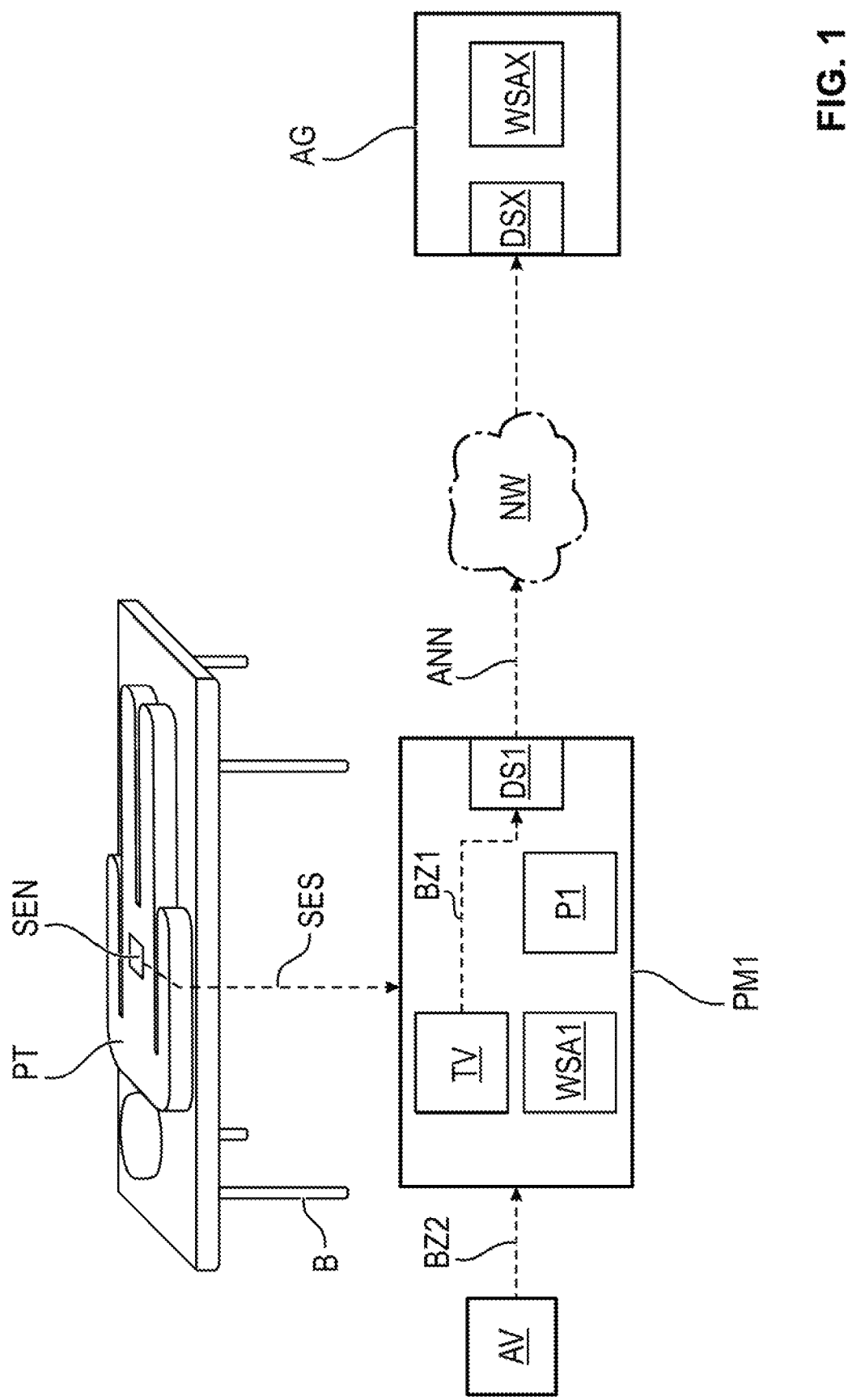
FIG. 1 is a view showing a scenario in a clinical setting.

Referring to the drawings, FIG. 1 shows a scenario in a clinical setting. A patient PT, who preferably lies on a patient positioning device in the form of a bed B, is monitored with respect to physiological data by means of a medical device PM1, which is preferably a patient monitor. In addition or as an alternative to the monitoring of physiological data, the device PM1 monitors an operating state of another technical device AV, which is, for example, another medical device. The device PM1 preferably monitors an operating state of an own partial device TV. The operating state is preferably an operating state of the partial device TV on or in the medical device PM1. For example, the medical device PM1 is a so-called patient monitor, where a signal BZ1 indicates which operating state is currently given for an ECG electrode connected to the patient monitor PM1 by means of an interface TV1, for example, whether the ECG electrode is positioned on a human body or whether the electrode is not positioned (any longer) on a human body. For example, the medical device PM1 is an infusion pump device, which checks a pressure in the corresponding tube system of the infusion pump device PM1 by means of a manometer TV1 and derives an operating state therefrom.

The operating state is preferably an operating state of another device AV, which differs from the medical device PM1. The signal BZ2 indicates here, e.g., on the patient monitor PM1 an operating state of the infusion pump device AV that is separate from the patient monitor PM1.

A signal SES, which indicates physiological measured values relative to the patient PT, is preferably provided by means of at least one sensor SEN when monitoring the physiological data. The device PM1 receives the signal SES via a corresponding interface.

When monitoring the operating state, the device PM1 receives a data signal BZ1, BZ2, which indicates an operating state of the device AV or of the partial device TV, from the device AV or from the partial device TV. Such an operating state is, for example, a "Ready," "Not Ready," "Standby," "ON," "OFF" or "ERROR" status.

A processor P1 monitors the physiological measured values or the operating state and detects, by comparison with at least one preset reference value, a state in which an alarming shall take place in order to alert a clinician or another hospital staff to the detected state. The device PM1 can preferably output for this the alarm via an alarm signal output unit WSA1 directly to the device PM1. Such an output in the direct proximity of the patient PT is possibly disadvantageous, because the patient PT may possibly be disturbed or bothered hereby. Further, it is possible that the door of the patient room is closed in a so-called closed-door scenario, so that the output of an alarm signal directly at the device PM1 via the unit WSA1 may not possibly be perceived by the clinician or the hospital staff. Therefore, a door of the patient room is at least left open in a clinical setting, but this compromises the resting situation of the patient and/or potentially exacerbates the hygienic situation.

It is known that the medical device PM1 does not perform the alarming via its alarm output unit WSA1 itself, but that the medical device PM1 sends a request message ANN to a data network interface DSX of an alarm device AG, which is located outside the patient room, via a data network interface DS1 via a data network NW. The message ANN represents a request to perform the outputting of an alarm signal on the alarm device AG via the own alarm signal output unit WSAX thereof.

It is further a possible scenario that more than one alarm device AG is present in the clinical setting. For example, there are so-called pagers for physicians; further, e.g., also alarm output devices, which are positioned in hallways or corridors, as well as further, e.g., alarm output devices, which are positioned in a central station room. If the device PM1 sent the same request message ANN simultaneously to a plurality of such alarm devices, an alarm signal would possibly be outputted simultaneously on all such alarm devices. The output of the alarm signals in an acoustic and/or optical form could as a result lead to overtaxing and excessive irritation of the hospital staff. Therefore, one goal of the present invention is to ensure the output of an alarm to alarm devices in a coordinated manner, where it should be possible to minimize the number of alarms outputted. Such a solution therefor would be that a medical device PM1 sends a detected alarm state to a central coordination unit in the network, which unit then coordinates the distribution of alarm signal requests to different alarm devices.

Figure 2:
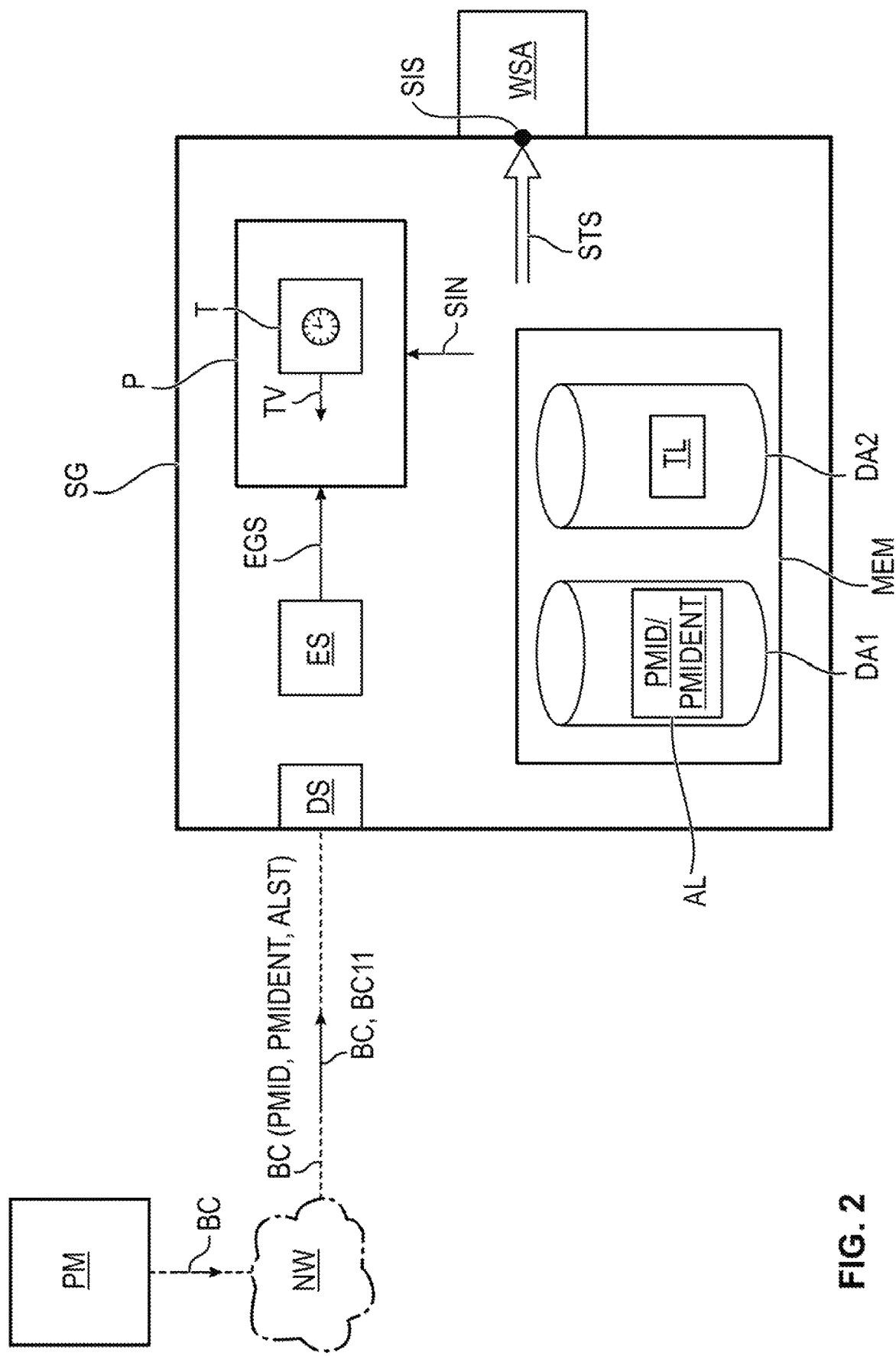
FIG. 2 is a view showing a medical device as well as a control device according to the present invention according to a first embodiment.

FIG. 2 shows the control device SG according to the present invention together with a medical device PM.

The medical device PM is configured essentially like the medical device PM1 explained above with reference to FIG. 1.

Further special embodiments of the medical device PM will now be explained in more detail with reference to FIG. 4.

The device PM has an alarm output unit WSA2. The device PM has further an input unit ES2 for generating an input signal EGS2 in case of actuation of the input unit ES2 by a user. The input unit ES2 is preferably a key, a push-button or a touchscreen.

Further, the device PM has an interface SEC for receiving a sensor signal SES, which indicates physiological measured values of a patient. A physiological measured value is, for example, a heart rate, a blood pressure or a blood oxygen level of a patient.

A data set DA11 which indicates at least one reference value R, is present or provided in a memory unit MEMP. Further, a second data set DA22 is provided, which indicates a first time period TM1 and a second time period TM2.

The device PM has further a data network interface DSP as well as a processor PR. The processor is set up to operate and provide a timekeeping function TP. The timekeeping function TP corresponds to a timekeeping function T of the control device SG from FIG. 2, which will be explained in more detail below.

The device PM preferably has a data interface DAS, via which the device PM receives the signal BZ2, which indicates as a data signal an operating state of the other device AV. The device PM preferably has further a partial device TV, which provides a signal BZ1, which indicates an operating state of the partial device TV, as was mentioned above. By comparing the operating state indicated in one of the signals BZ1, BZ2, the presence of a state of alarm can then be detected by comparison with a reference value R. For example, the reference value R is a list, which indicates operating states in the presence of which a state of alarm is said to be given or shall be detected.

By comparing the physiological measured values received at the interface SES and a corresponding reference value R, the processor PR can detect whether an alarm state is present. If, e.g., the reference value R is a threshold value and a recorded physiological measured value exceeds the reference value or threshold value, the presence of the alarm state is then detected by the processor PR. An alarm state is given, for example, if the physiological measured values indicate a pulse of the patient and if the maximum pulse as a reference value R is exceeded. Further embodiments for detecting states of alarm by comparisons of physiological measured values and corresponding reference values are conceivable and understandable to the person skilled in the art.

The detection of a state of alarm on the basis of one of the signals BZ1, BZ2, which indicate each an operating state, can take place as described above.

The processor PR is further configured to send a first group message BC, which indicates the presence of the alarm state, to additional network participants via the data network interface DSP in the presence of the alarm state or if the alarm state is detected. The group message BC is preferably a broadcast message BC according to this example. The group message BC contains at least the network identity PMID of the sender PM sending the message BC as well as a data element ALST, which indicates the alarm state. The group message BC preferably contains identification data PMIDENT, which identify the device PM sending the message BC. The group message BC is sent into a network NW. The data network interface DSP is further configured to send or to receive additional messages, as it will be explained in more detail below. The identity PMID may be a network address or network identity, e.g., an IP address of the device PM. As an alternative, the identity PMID is a data element which unambiguously identifies the device PM.

The group message BC in the sense of this application is a data network message. Such a group message is a data network message, which is sent to one or more network units of a group of network units. The group of network units is then preferably defined by group identification data, e.g., a multicast address or a quantity of a plurality of respective data network addresses of respective network units. A group message in the sense of this application is consequently a data network message of the type of a broadcast message, an anycast message, a multicast message or one or more unicast messages.

The group message BC is preferably sent to the network units that are indicated by group identification data SGID of the data set DA3.

The device PM preferably has an own alarm output unit WSA2, which can be actuated by the processor PR by means of a control signal STSP for outputting an alarm signal.

The memory unit MP preferably provides a data set DA3, which indicates a list with network participant identities SGID or network identities of control devices, which can, in principle, receive the group messages BC. If the data set DA3 is an empty data set, the processor PR can infer that no control device had logged in before at the device PM by means of a log-in process and that no control device is consequently actuating or generating the outputting of an alarm, so that the processor actuates the outputting of an alarm at the device PM itself. The processor PR outputs for this a control signal STSP to the alarm output unit WSA2 of the device PM.

FIG. 2 likewise shows the medical device PM with the group message BC, which is sent via the network NW to a data interface DS of the control device SG.

As is shown here in FIG. 2, the control device SG has, according to the present invention, an alarm signal output unit WSA itself, via which an optical and/or acoustic alarm signal can be outputted. Further, as will be explained later with reference to FIG. 3, it is possible, as an alternative, that in a second embodiment, the control device SG11 shown there does not have the alarm signal output unit itself, but another network participant MO of another network NW2 has an alarm signal output unit WSAM. This will be explained in more detail later with reference to FIG. 3 within the framework of the second exemplary embodiment.

An alarm signal output unit in the sense of the patent application is an output unit for outputting an optical and/or acoustic warning. An alarm signal output unit may thus be, for example, an optical display element and/or an acoustic output element, e.g., a loudspeaker, a buzzer or a horn.

The control device SG from FIG. 2 has a signaling interface SIS for outputting a control signal STS, which indicates a request for outputting an acoustic and/or optical alarm signal. The control device STS preferably contains here the Boolean value 1 for the indication of the request.

In the sense of the present application, a control signal may be an electrical signal, such as a current or a voltage. The control signal is preferably a data signal for sending via a wired network or a wireless network.

The control device SG has at least one memory unit MEM. Further, the device SG has a processor P, which is configured to operate or provide a timekeeping function T. The timekeeping T may be a so-called stop watch, or else, for example, a usual time function for time measurement. The timekeeping function provides the time values TV.

The control device receives the group message BC via the data interface DS. The message BC indicates as the sender address the network identity or network address PMID of the sender PM. This network identity is a possibility of a sender identity of the sender. The message BC preferably indicates, as an alternative or in addition, identification data PMIDENT as a sender identity of the sender.

The message BC consequently indicates a sender identity PMID, PMIDENT of the sender PM as well as the presence of the alarm state by means of the status data element ALST.

The memory unit MEM provides a data set DA1, which indicates a list AL with potential sender identities PMID, PMIDENT. The potential sender identities PMID, PMIDENT may be network addresses or network identities PMID of senders and/or identification data PMIDENT of senders. The memory unit MEM has further a data set DA2, which indicates time periods, during which an alarm signal shall possibly be outputted. These time periods are preferably indicated by a list TL. The indicated time periods have, at least implicitly, a beginning and an end.

The processor P outputs the control signal STS as a function of an agreement of the sender identity PMID indicated in the group message BC with a sender identity PMID indicated in the first data set DA1. Further, the processor P outputs the control signal STS as a function of a comparison of a current value TV of the timekeeping function T and of the time periods that are indicted in the second data set DA2. This will be explained in more detail later with reference to FIGS. 7a through 7b.

The control device has further an input unit ES for generating an input signal EGS in case of actuation of the input unit ES by a user. The input unit ES is preferably a key, a pushbutton or a touchscreen.

The processor P is further configured to receive a status information SIN, which indicates whether an alarm output unit WSA can be reached by a control signal STS.

The control device SG according to the present invention, which is a device in the sense of the alarm device AG from FIG. 1, as well as the method according to the present invention make it possible to execute out the output of an alarm by means of a plurality of alarm devices in a coordinated manner, wherein the alarm outputs can be minimized. No central unit is necessary in the network between the medical device PM1 and the alarm output devices AG for outputting an alarm in a coordinated manner.

Figure 7A:
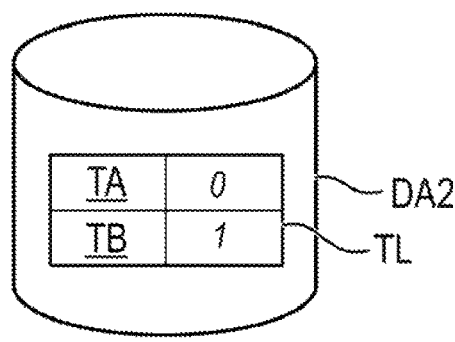
FIG. 7a is a schematic view showing a data set.
Figure 7B:
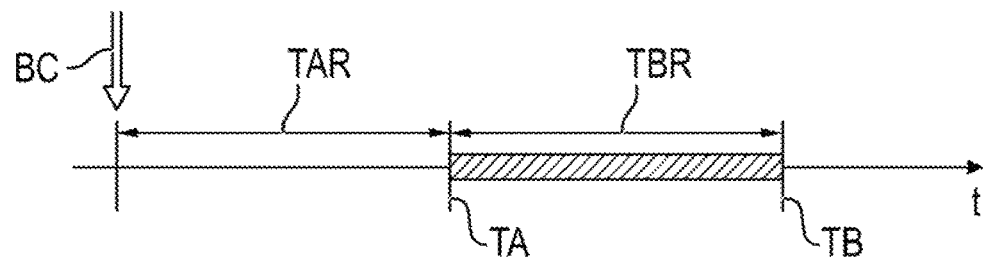
FIG. 7b is a graphic diagram of time periods.

FIG. 7a shows for this once again the data set DA2 in detail with a list TL, which indicates for respective time values TA and TB starting from the receipt of a group message and hence implicitly for respective time periods whether an alarm signal shall be outputted or not. This is preferably indicated on the basis of Boolean values 0 and 1. The respective time values TA, TB consequently indirectly indicate time periods starting from the arrival of a first group message BC, during which an alarm signal shall be outputted. FIG. 7b illustrates for this these time periods TAR and TBR, which can be determined by applying the time values TA and TB indicated from the list TL. A timekeeping function or a stop watch function is started on arrival of the group message BC and an alarm is outputted depending on a time value of the timekeeping function as well as on the time values TA, TB. As an alternative, the timekeeping function is a continuously running timekeeping function, and the outputting of an alarm is made contingent upon a time value of the timekeeping function on arrival of the group message BC, a current time value of the timekeeping function as well as on the time values TA, TB.

The indicated time period TAR has a beginning time on arrival of the message BC and an end time at the time TA. The indicated time period TBR has a beginning time at the time TA and an end time at the time TB.

The alarm signal shall be outputted in this example from the time TA to the time TB during the time period TBR. An alarm is outputted in this example during the time period TBR such that a control signal output for generating or requesting an alarm signal is suppressed at the latest at the end of the time period TBR.

It is clear to a person skilled in the art that the variant of indicating the time periods TAR, TBR, which is selected here, by means of the time values TA, TB and the Boolean values 0 and 1 is only an example for an implementation of the control device according to the present invention and of the method according to the present invention.

The advantage of the control device according to the present invention and of the method according to the present invention is that the medical device PM shown in FIG. 2 must communicate only the presence of the alarm state via the group message BC to alarm devices and control devices SG and that the alarm devices or control device SG are then correspondingly preconfigured in themselves based on their data sets DA2 to cause the output of an acoustic and/or optical alarm at very specific time periods TBR. As a result, a control device SG can consequently be assigned to corresponding alarm classes or device groups in a simple manner by means of a modification of the corresponding data set DA2, so that an alarming is not performed by all the control devices SG communicating with the medical device PM during equal time periods, but they can cause the outputting of an acoustic and/or optical alarm signal, for example, staggered in time, during time periods TBR of their own.

Figure 7C:
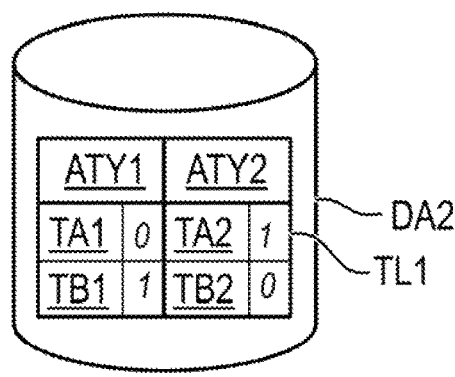
FIG. 7c is a schematic view showing a data set.
Figure 7D:
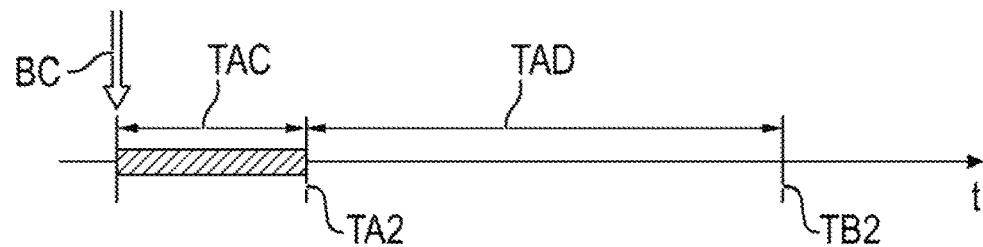
FIG. 7d is a graphic diagram of time periods.

FIG. 7c shows an alternative embodiment of the data set DA2 with a list TL1. The list TL1 contains here, for a first alarm type ATY1, data that indicate time periods, as was explained above with reference to FIGS. 7a and 7b. Further, the list TL1 contains data for a second alarm type ATY2, and these data indicate additional time periods concerning an alarm output. The time periods TAC, TAD are shown in FIG. 7d. This embodiment of the present invention is advantageous, because it is thus possible to make the output of an alarm signal on the control device SG also contingent upon the kind of alarm type indicated by a received group message BC, As a result, the control device SG from FIG. 2 may consequently have different alarming characteristics for different types of alarm. An alarm is outputted in this example during the time period TAG such that a control signal output to generate or request an alarm signal is suppressed no later than at the end of the time period TAC.

The control device according to the present invention preferably uses a data element ATY provided in a group message, see FIG. 6 with the group message BC11, which will be explained in more detail later, in order to infer a very specific type of alarm. The control device according to the present invention preferably has an additional provided data set, which indicates respective types of alarm for respective values of the data element ATY, e.g., "high blood pressure alarm," "pulse rate alarm" or similar types of alarm.

Figure 4:
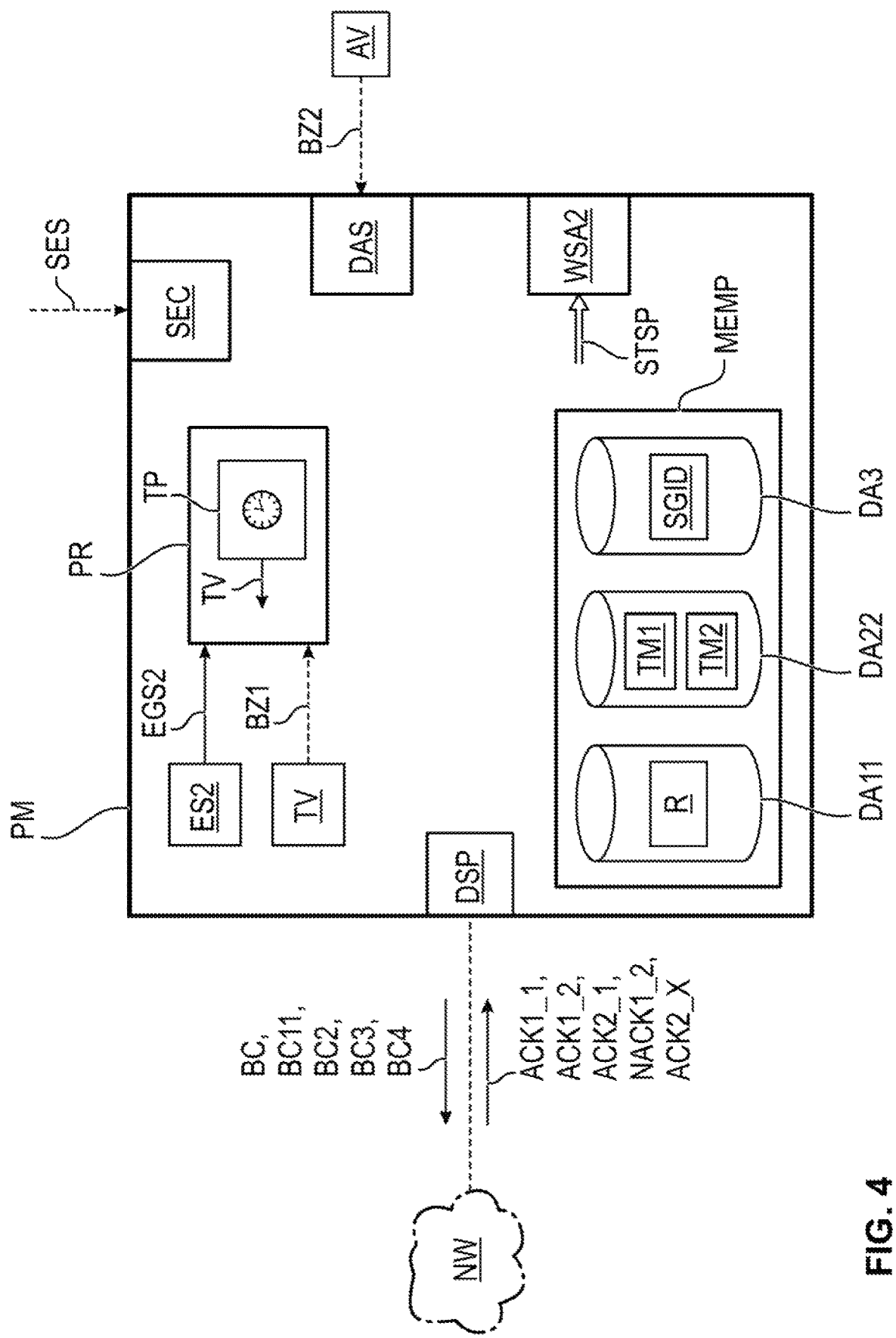
FIG. 4 is a view showing a medical device according to the present invention.
Figure 5:
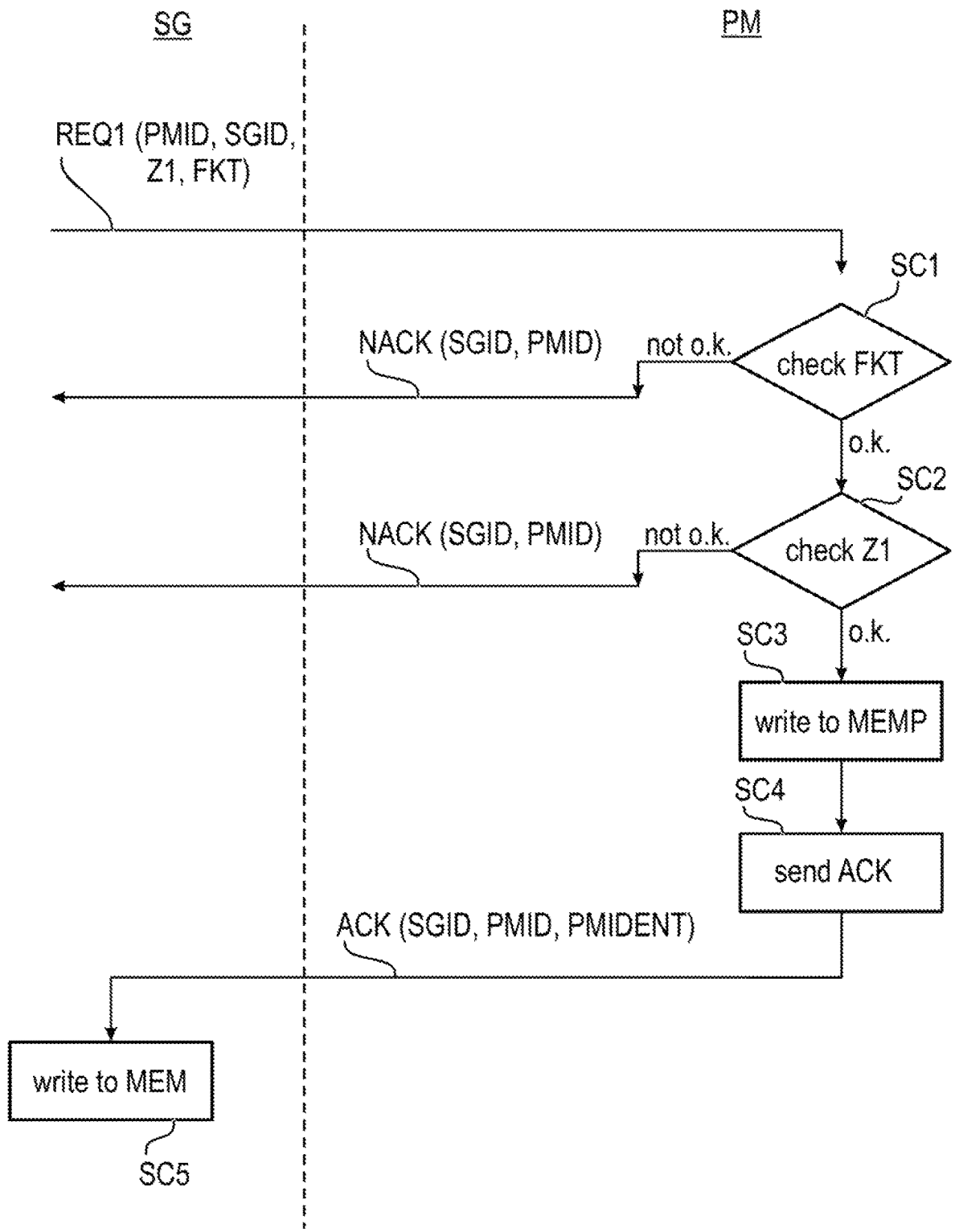
FIG. 5 is a view showing steps of a method for assigning a control device to a medical device.

FIG. 5 shows steps of a log-in process, with which a control device SG from FIG. 2 can log in or register in a medical device PM from FIG. 4 in order to then be assigned to the medical device PM.

A request message REQ1 is first sent by the control device SG to the device PM, which has as the target address the network identity PMID of the device PM; further, it has as the sender address the network identity SGID of the control device SG; further, certificate data Z1 as well as further a data element FKT, which indicates a functionality of the control device SG.

After receiving the request message REQ1 at the device PM, the device PM checks in a step SC1 whether the indicated functionality FKT of the sender SG of the request message REQ1 is permissible. If yes, there is a further branching to a step SC2. If this is not the case, a rejection message NACK is sent back to the control device SG. It is checked in step SC2 on the basis of the certificate data Z1 whether a log-in or registration of the control device SG on the device PM is permissible. If not, a rejection message NACK is sent to the control device SG. If this is permissible, the identity SGID of the control device SG logging in is stored in the device PM in a data set DA3. As a result, the device PM from FIG. 4 stores information on control device SG that are logged in to it for controlling the output of an alarm. The device can possibly infer from this that the outputting of an alarm can be brought about, in principle by outputting an alarm by sending a group message BC.

If the control device SG has successfully logged in to the device PM, an acknowledgment message ACK is sent to the control device SG in a step SC4. This message ACK contains the network identity SGID of the control device as a target address and the network identity PMID of the device PM as a sender address. The network identity PMID can then be stored as a potential sender identity in the memory MEM of the device PM. The message ACK preferably contains identification data PMIDENT, which unambiguously identify the device PM, and is then preferably stored as a potential sender identity in the memory MEM of the device PM.

Then, after receipt of the acknowledgment message ACK in the control device SG, either the network identity PMID of the device PM or the identification data PMID of the device PM are stored in step SC5 in the data set DA1, preferably by means of a list AL, as was already mentioned in FIG. 2. As a result, it is then consequently known to the control device SG to which group message BC of which medical device PM it must respond with which sender identity PMID or PMIDENT for the purpose of outputting an alarm.

Figure 6:
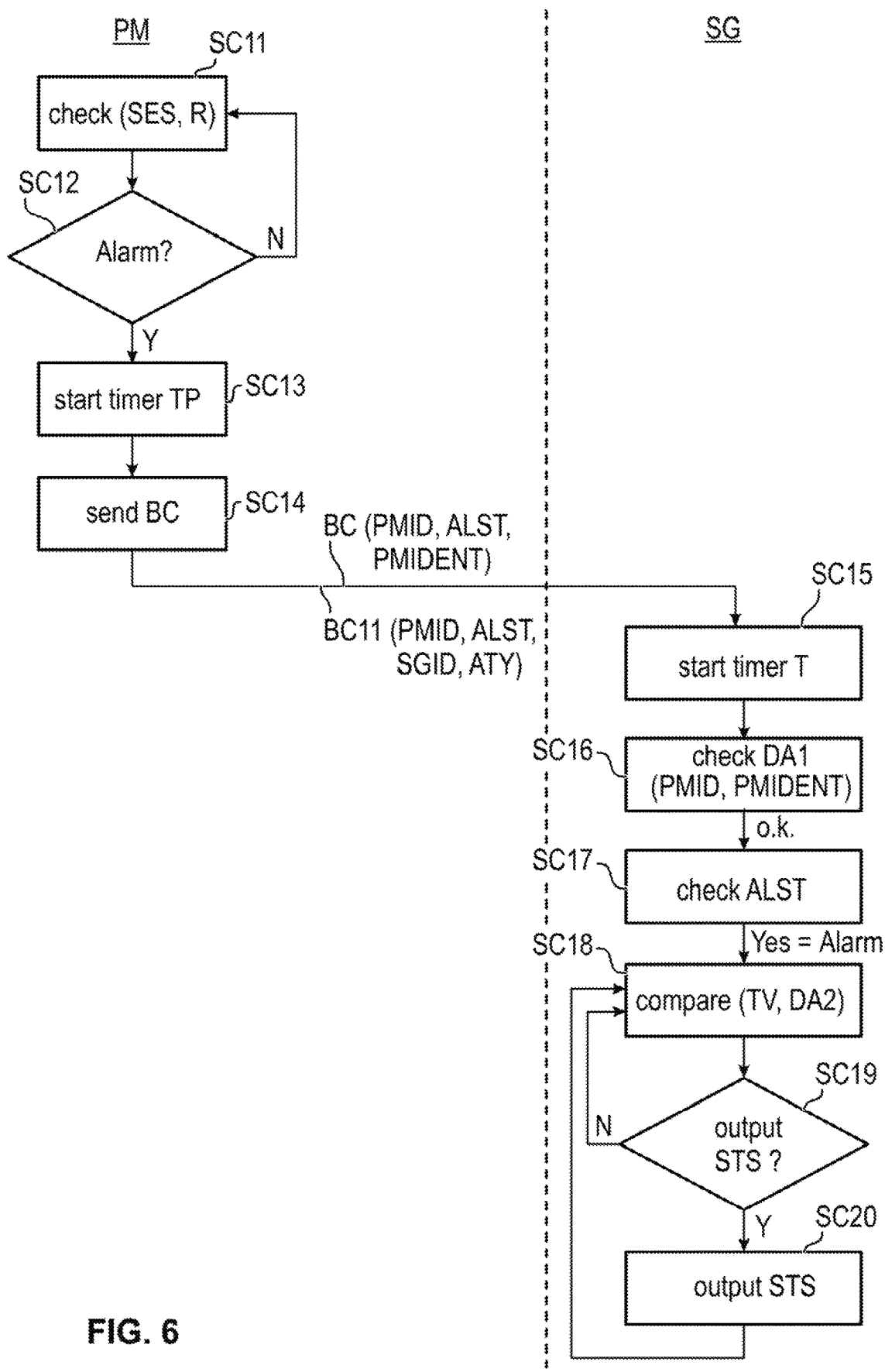
FIG. 6 is a view showing steps for executing the method according to the present invention.

FIG. 6 shows method steps for executing the method according to the present invention and for explaining the mode of operation of the control device according to the present invention in more detail. It is obvious to the person skilled in the art that the steps described with reference to FIG. 6 can be executed by respective processors with the use of additional, above-mentioned partial devices.

In a method step SC11, the medical device PM checks whether or not an alarm state can be detected on the basis of the physiological measured values SES and the reference values R. In case an alarm state is to be detected, the process is branched in the next step SC12 to a method step SC13, in which the medical device PM itself preferably starts its own timekeeping function TP, whose function will be explained in more detail below.

In a step SC14, the device PM then sends the group message BC, which indicates the identity of the sender, e.g., in the form of the network identity PMID. In the preferred case in which the network identity PMID itself is used as the sender identity, the group message BC has further sender identity data PMIDENT.

The group message has further a data element ALST, which indicates the presence of the alarm state.

The first group message is preferably given in the form of an alternative first group message BC11, which further contains, compared to the group message BC, a data element ATY, which indicates an alarm type.

The control device SG preferably starts its timekeeping function T, which is a stop watch function in this example, in a step SC15 after receipt of the group message BC, BC11.

In a next step SC16, the device SG checks whether the sender identity PMID, PMIDENT of the first group message BC, BC11 agrees with a potential sender identity PMID, PMIDENT from the data set DA1, see FIG. 2. A checking is consequently performed to determine whether the first group message BC, BC11 originates from a medical device PM, to which the control device SG is assigned. It is made possible hereby that the device PM does not have to address any explicit control devices in the message BC, BC11 in order to initiate an alarm output to such control devices SG only.

If the checking performed in step SC16 has a positive result, it is checked in a next step SC17 whether the alarm state ALST is given or indicated.

If yes, it is determined in a next step SC18 by comparing a value TV of the timekeeping function T and the time periods indicated in the data set DA2 whether or not a control signal STS shall be outputted at the moment or currently.

In case no control signal STS shall be outputted, the process is branched back in a next step SC19 to the step SC18. However, if a control signal STS shall be outputted, the process is branched to a method step SC20, in which the control signal STS is outputted.

The process is then branched back from step SC20 to step SC18 in order to check continuously whether the control signal STS shall be outputted.

Figure 8:
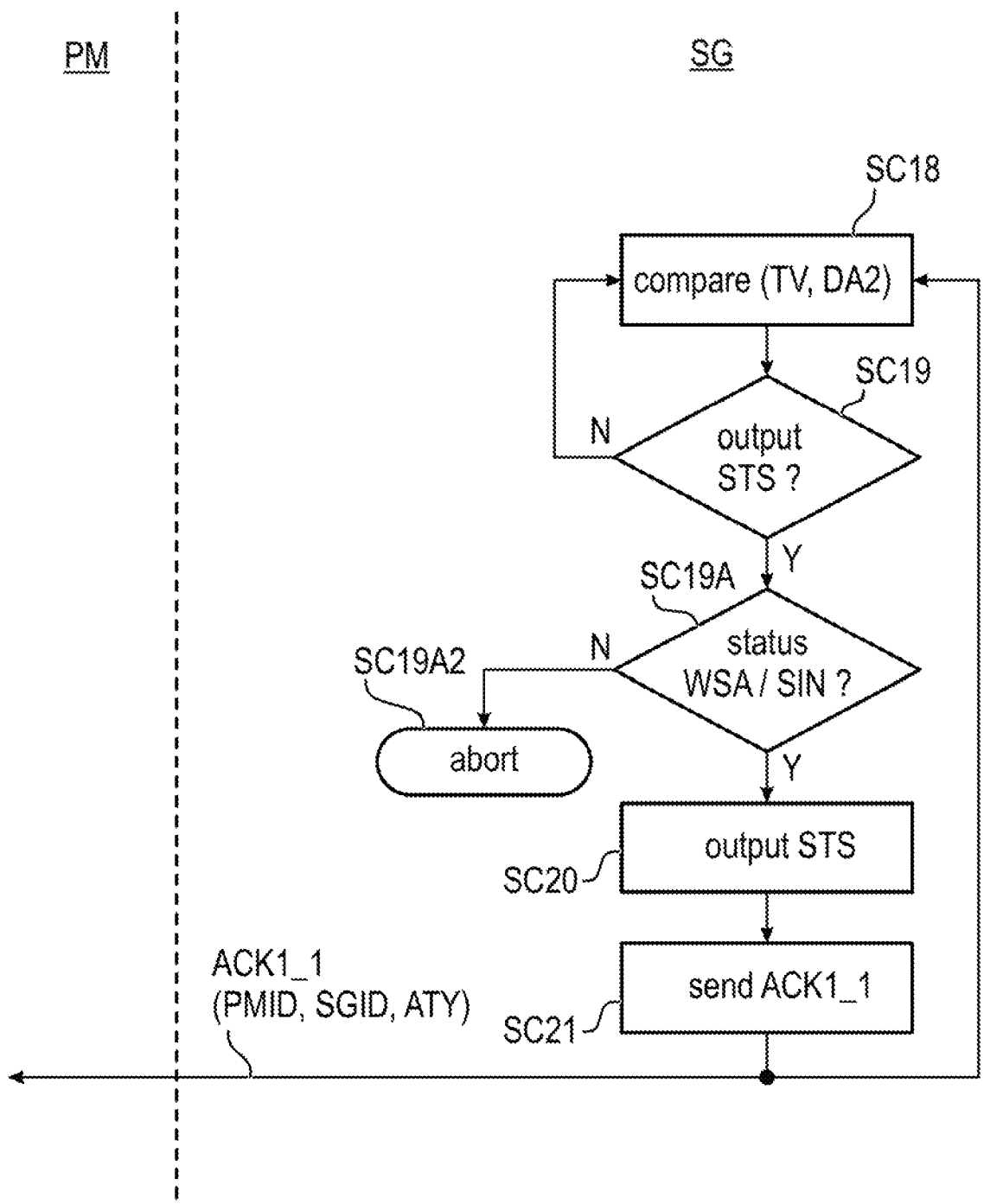
FIG. 8 is a view showing method steps within the framework of a checking to determine whether a control signal of an alarm signal output unit can reach an alarm signal output unit.

FIG. 8 shows further signals as well as further method steps, on the basis of which further functionalities are brought about in interaction with the method steps SC18, SC19 as well as SC20 described hitherto with reference to FIG. 6. It is made possible hereby that a checking is performed to determine whether the outputting of the control signal STS can reach an alarm signal output unit PSA at all.

The status information SIN shown in FIG. 2 can be used to check whether or not the alarm output unit WSA according to FIG. 2 is capable of outputting an alarm signal at all.

The status information SIN preferably indicates here an operating state of the unit WSA; as an alternative, the status information SIN indicates whether the unit WSA is connected to the control device SG at all.

Thus, an operating status of the unit WSA is detected or determined in the method step SC19A. If the status of the output unit WSA indicated by the status information is such that the control signal will be able to successfully reach the unit WSA through the control signal, the process proceeds further to method step SC20, in which the outputting of the control signal STS is brought about. If the control signal STS cannot successfully reach the output unit WSA, the process is branched off to a method step SC19a2, in which the method is interrupted.

A first status message ACK1_1 is sent in a method step SC21 to the sender PMID that was the sender PMID of the group message BC. The index "1_" following "ACK" indicates here in this example that this is a first status message or a status message of a first type. The further, last index "1" indicates that the message was sent by a first control device. The status message ACK1_1 preferably has a data element ATY, which was described before with reference to the message BC11 according to FIG. 6. The type of alarm, to which the status message applies, is indicated by the data element ATY. As a result, the individual messages, such as the group message BC11 and the status message ACK1_1, can be used each for certain types of alarm separately and a distinction can thus be made between different types of alarm.

The status message ACK1_1 informs the sender PM of the group message BC that an alarm output unit WSA can be successfully actuated and that an alarm is thus outputted.

Figure 9A:
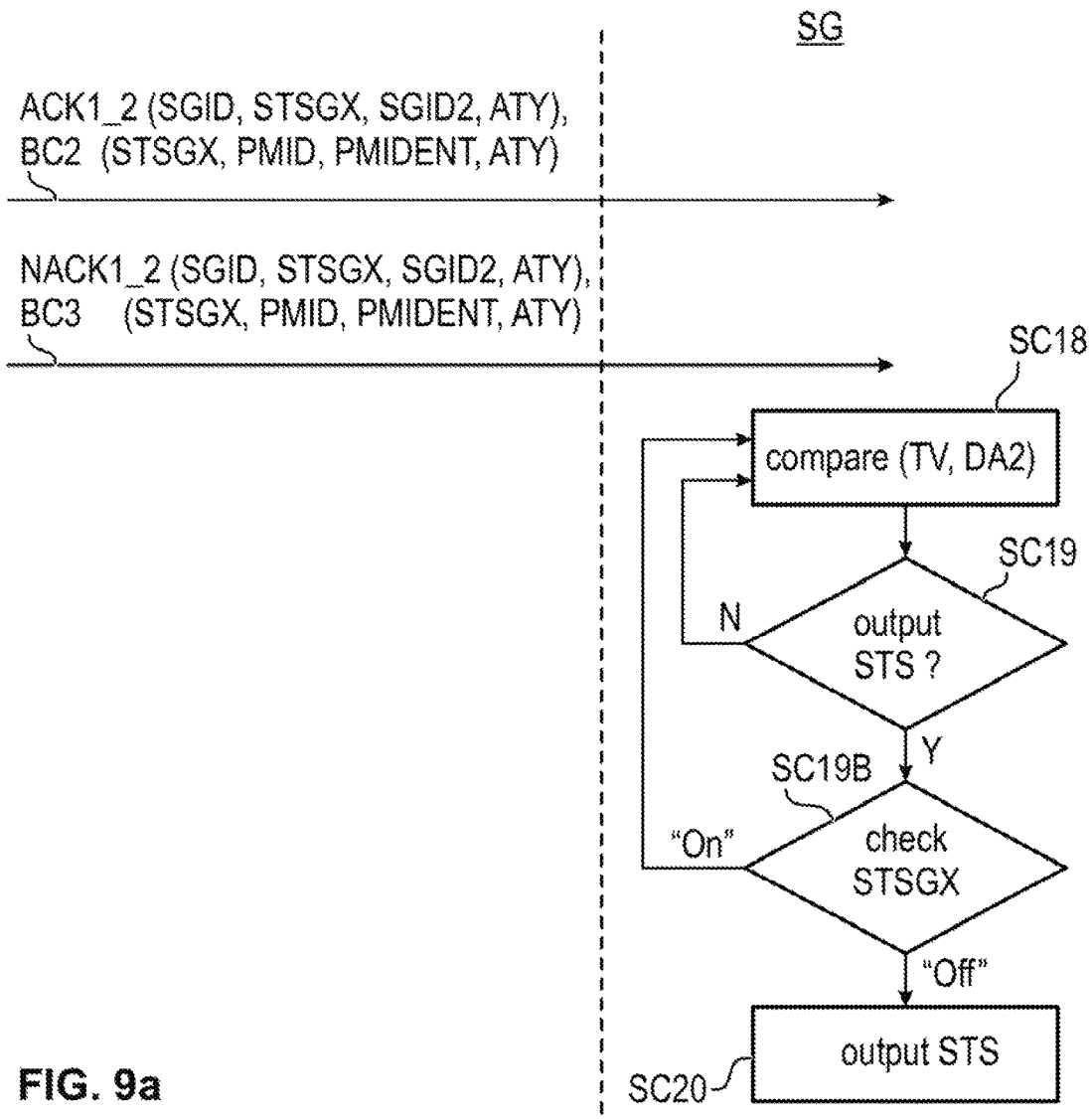
FIG. 9a is a view showing method steps, by means of which the outputting of a control signal is performed as a function of the presence of a status message.
Figure 9B:
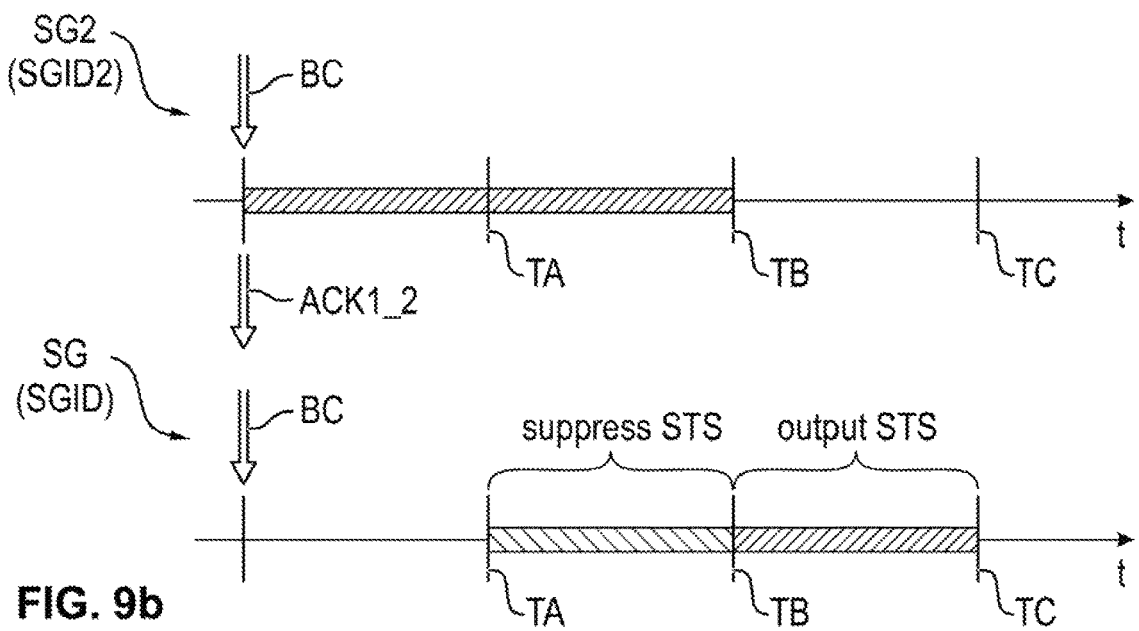

FIGS. 9a and 9b show additional signals as well as additional method steps, on the basis of which additional functionalities can be brought about in interaction with the method steps SC18, SC19 as well as SC20 described hitherto with reference to FIG. 6. It is clear to the person skilled in the art that a combination of the method steps according to FIG. 9a with those according to FIG. 8 is also possible, so that additional functionalities can be obtained.

FIG. 9a shows an additional method step SC19B. The control device SG receives via its data network interface a first status message, which is a group message BC2 in this case, which indicates in a data element STSGX whether another control device is successfully actuating an alarm signal output unit. An aforementioned medical device PM can analyze, for example, by analyzing a first status message ACK1_1 from FIG. 8, that another control device is successfully actuating an alarm signal output unit and then initiate the sending of a first status message in the form of the group message BC2. The group message BC2 preferably has a data element ATY for indicating a certain type of alarm, as was explained in more detail above with reference to FIGS. 6 and 8.

As an alternative to a first status message in the form of the group message BC2, a first status message ACK1_2 sent directly from another control device—with a corresponding identity SGID2—can also be received at the control device SGID, which status message likewise indicates that the control device with the identity SGID2 is successfully performing the outputting of an alarm signal.

The output of the control signal STS can then be made contingent in the method step SC19B on whether the data element STSGX indicates that an alarm signal is already being successfully outputted by another control device. If so, no control signal STS is outputted at the control device SG itself; therefore, the process is not branched off to the method step SC20. This is advantageous, because in case another control device is already outputting the alarm signal, the control device SG itself will then stop its own actuation STS for outputting an alarm signal.

If the control device SG later receives a second status message in the form of a group message BC3, which indicates by means of a data element STSGX that the other control device is no longer performing an actuation of an alarm signal output, a decision is then made in step SC19B that the process is nevertheless to be branched to step SC20, and the control signal STS is outputted in step SC20. The group message BC3 preferably has a data element ATY for indicating a certain type of alarm, as it was explained in more detail above with reference to FIGS. 6 and 8.

As an alternative to the second status message in the form of the group message BNC3, a second status message NACK1_2 sent directly by another control device, with a corresponding identity SGID2, which likewise indicates that the other control device with the corresponding identity SGID2 is no longer performing the outputting of an alarm signal, can also be received at the control device SGID. The status message NACK1_2 preferably has a data element ATY for indicating a certain type of alarm, as it was explained in more detail above with reference to FIGS. 6 and 8.

These possibilities of control signal output, which were discussed with reference to FIG. 9a, are illustrated in FIG. 9b in more detail. Time periods up to the times TA and TB, at which the control device SG2 shall output the alarm signal, are indicated for another control device SG2 being assumed here, which has the above-mentioned identity SGID2.

With the beginning of the output of the alarm signal, the control device SG2 sends its first status message ACK1_2, which is possibly received directly by the control device SG. As an alternative to this, the medical device PM receives the status message ACK1_2 and then sends a status message BC2, as it was explained above.

Even though the data sets being stored in the memory unit of the control device SG indicate in themselves that a control signal is to be outputted starting from the time TA to a time TC for requesting the output of an alarm signal, the control unit SG can nevertheless suppress its output of the control signal SCS in the manner described above with reference to FIG. 9a from the time TA to the time TB, because it is informed that the other control device SG2 is already performing an alarm signal output based on the first status message ACK1_2, BC2. The output of an alarm signal is therefore suppressed on the control device SG from the time TA to the time TB.

Since the control device SG2 sends the above-described second status message NACK1_2 at the time TB and either this second status message NACK1_2 or a second status message sent by the medical device PM in the form of the group message BC3 is received at the control device SG, the control device SG will still nevertheless output a control signal for requesting the output of an alarm signal starting from the time TB up to the time TC. The output of the control signal is suppressed no later than at the end of the time period that ends with the time TC.

Figure 10A:
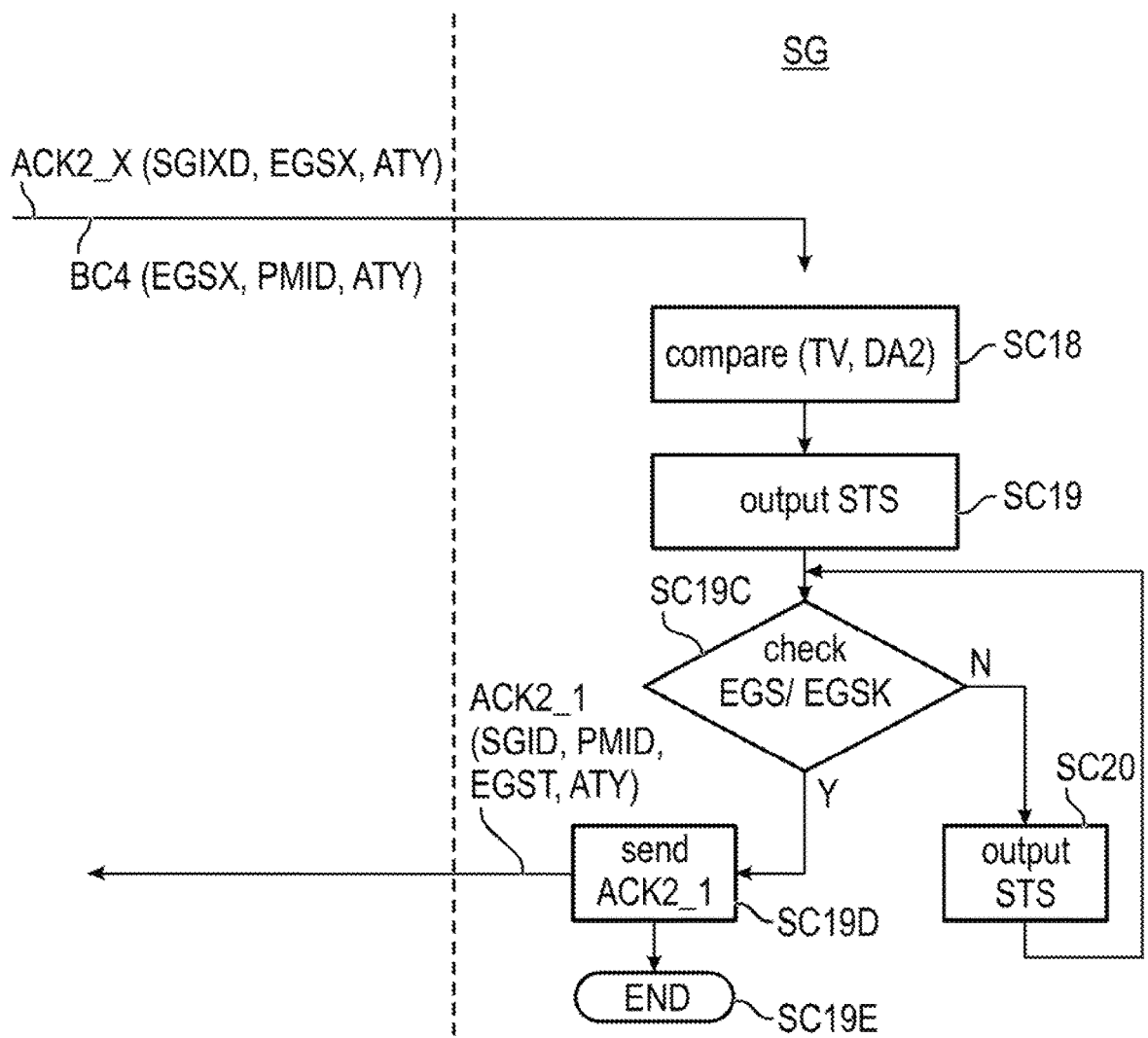
FIG. 10a is a view showing method steps within the framework of a checking to determine whether an acknowledgment of an alarm signal was performed by an input by a clinician on a control device, the output of the control signal preferably being suppressed.
Figure 10B:
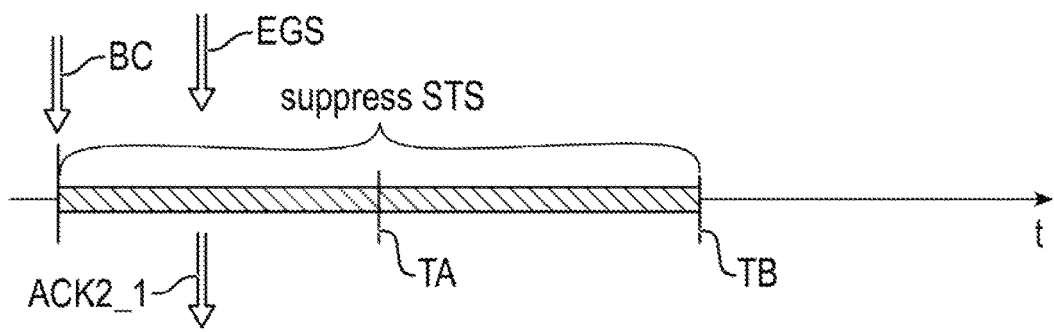

FIGS. 10a and 10b show additional signals as well as additional method steps, on the basis of which additional functionalities are brought about in interaction with the method steps SC18, SC19 as well as SC20 described hitherto with reference to FIG. 6. It is clear to a person skilled in the art that a combination of the method steps according to FIG. 10a with those according to FIG. 8 and/or according to FIG. 9a is also possible, so that additional functionalities can be obtained.

FIG. 10a shows additional method steps, by means of which the possible presence of an input signal which indicates an acknowledgment of an alarm by a user can be taken into account.

The control device shown in FIG. 2 has an input interface ES for receiving an input signal EGS, which indicates an acknowledgment of the alarm signal by a user. The processor P can then check, if the input signal EGS is present, by the step SC19C according to FIG. 10a, whether an input was made by a user. If not, the alarm was not acknowledged or confirmed by a user, so that the control signal STS continues to be outputted in the course of the step SC20.

If, however, the alarm was acknowledged, so that the input signal EGS is present, the process is branched off in step SC19C to the step SC19D, in which a status message ACK2_1 is sent. This status message ACK2_1 indicates in a data element EGST that an acknowledgment of the alarm was performed or detected due to an input by a user on the control device SG. The status message ACK2_1 preferably has a data element ATY for indicating a certain type of alarm, as it was explained in more detail above with reference to FIGS. 6 and 8.

This information or the data element EGST can then be analyzed by the aforementioned medical device PM or the processor PR thereof in order to affect the output of an alarm signal on the medical device PM itself or else on other control devices.

FIG. 10b illustrates in this connection the output of a control signal for requesting the output of an alarm signal on the device SG, the output of the control signal STS being suppressed until the time period TB in the presence of the input signal EGS. If there is no input signal EGS, the output of the control signal is suppressed no later than at the end of the time period that ends at the time TB. Further, a third status message ACK2_1 is also sent at the time at which the input signal EGS is present. This third status message ACK2_1 can be sent to the medical device PM or directly to other control devices. The device PM can then perform the sending of a third status message in the form of a group message BC4 when receiving the third status message ACK2_1.

In a preferred embodiment, the control device SG receives from another control device a third status message ACK2_X, which indicates in a data element EGSX that an input of a user is present as an acknowledgment of the alarm at the sender SGXID. The device SG preferably receives this information by means of a group message BC4 of the medical device PM. The status message ACK2_X preferably contains a data element ATY for identifying a certain type of alarm, as it was explained in more detail above with reference to FIGS. 6 and 8.

The information in the form of the data element EGSX can then be used within the framework of step SC19 to suppress the output of the control signal based on the indicated acknowledgment of the user on the control device SG and not to branch off the method to the method step SC20.

Figure 3:
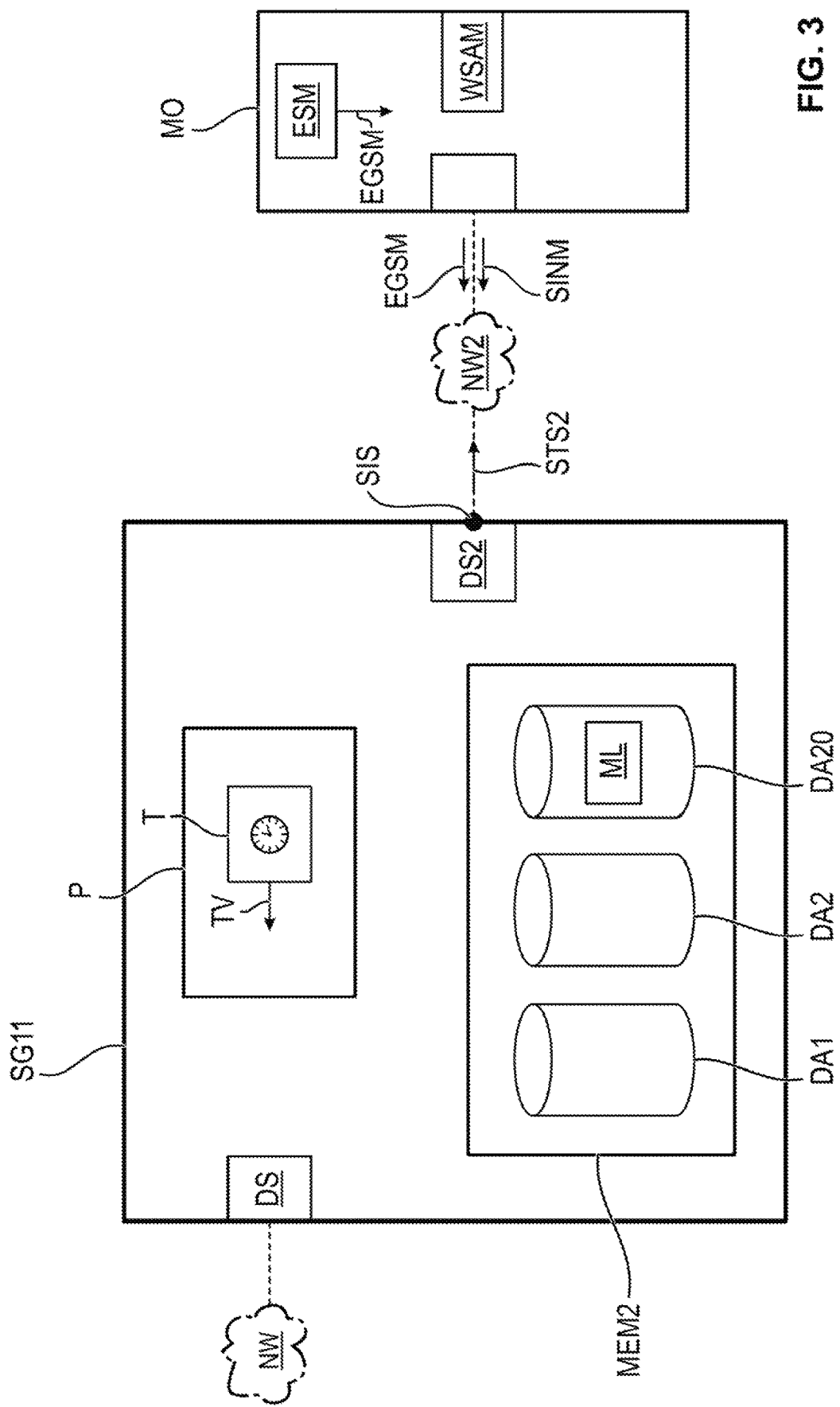
FIG. 3 is a view showing a control device according to the present invention according to a second embodiment as well as a network participant of a second data network.

FIG. 3 shows an alternative control device SG11, which has essentially the same configuration as the control device SG in FIG. 2. Differences between the control devices SG and SG11 will now be explained.

The control signal or signaling interface IS is configured in the control device SG11 as a second data network interface DS2, so that the control signal STS2 is sent as a data signal via a second data network NW2 to a mobile participant. It is possible as a result that the control device SG11 assumes a gateway functionality between the aforementioned first network NW and the second network NW2. The control signal STS2 is consequently sent to a mobile device MO, which has an alarm signal output unit WSAM of its own. Further, the mobile unit MO as an alarm output device has a data interface DSM to the network NW2.

Further, the mobile unit MO has an input interface ESM for receiving an input signal EGSM, which is sent via the network NW2 to the device SG11. Further, the mobile part MO is configured to send a status signal SINM relative to the alarm output unit WSAM to the device DS2 via the network NW2.

If the mobile part MO receives the control signal STS2, it outputs an alarm signal via its alarm signal output unit WSAM.

The processor P of the device SG11 controls the output of the control signal STS2 taking into account the signals EGSM, SINM now received via the interface DS2 in the manner described above within the framework of the first exemplary embodiment.

The control device SG11 preferably has in its memory unit MEM2 a data set DA20, in which a list ML with identities of network participants of the second data network NW2 is indicated. As a result, the control device SG11 has information on which network participants MO of the second data network NW2 it must send the control signal STS2.

Further aspects of the medical device PM will be explained now in more detail with reference to FIG. 4. The device PM has the data network interface DSP, which is configured to send the different group messages BC, BC11, BC2, BC3, BC4. Further, the different status messages ACK1_1, ACK1_2, ACK2_1, NACK1_2, ACK2_X can be received via the data network interface DSP. These different messages BC, BC11, BC2, BC3, BC4, ACK1_1, ACK1_2, ACK2_1, NACK1_2, ACK2_X were explained in more detail above with reference to the preceding figures.

The processor PR now analyzes received status messages ACK1_1, ACK1_2, ACK2_1, NACK1_2, ACK2_X in the above-described manner and generates depending on this the messages BC2, BC3, BC4 to be outputted.

A status message ACK1_1, ACK1_2, ACK2_1, NACK1_2, ACK2_X is now preferably taken into account only if the sender address or the network identity of the sender of the status message ACK1_1, ACK1_2, ACK2_1, NACK1_2, ACK2_X agrees with a network identity SGID of the data set DA3.

A first time period TM1 as well as a second time period TM2 are identified in the data set DA22.

Figure 11A:
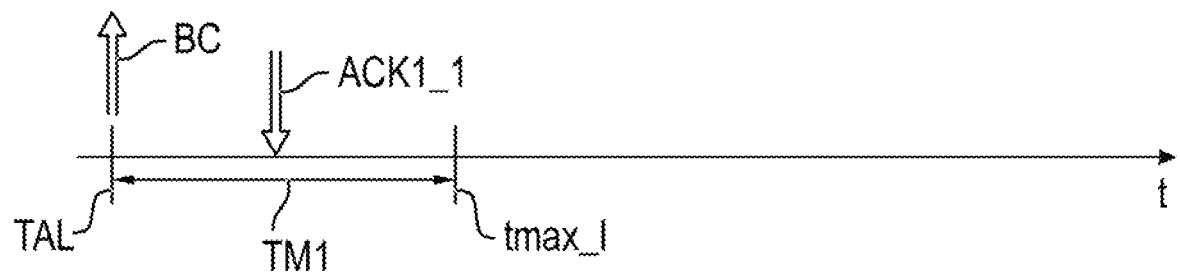
FIG. 11a is a view showing a first time period.
Figure 11B:
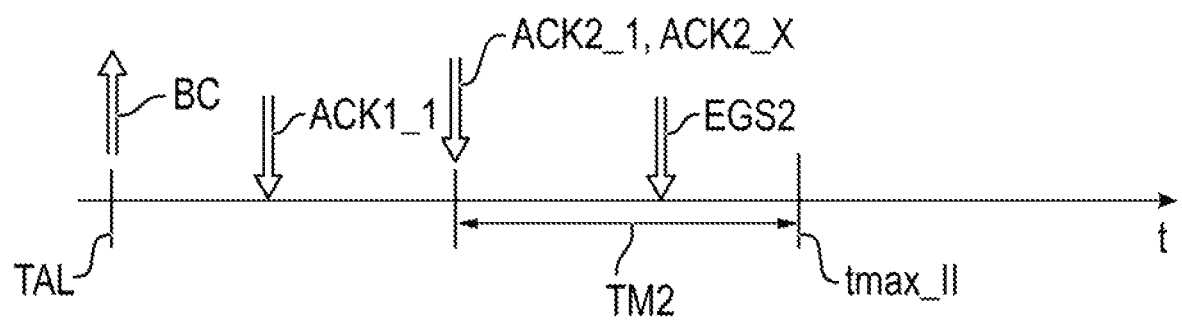
FIG. 11b is a view showing a second time period.

These time periods are explained in more detail in FIG. 11a and in FIG. 11b and are to be considered corresponding to FIGS. 2, 3 and 4.

FIG. 11a shows a time curve starting from a time TAL, at which a state of alarm is detected by the processor PR of the device PM. The group message BC explained in more detail above is sent at this time by the device PM.

The purpose of the first time period TM1 is that the processor PR of the device PM can decide whether it should possibly perform the output of the control signal STSP itself to the own warning signal or alarm output unit WSA2.

The processor PR therefore waits for the time period TM1 until the time tmax_I whether a first status message ACK1_1 described above in detail is sent by a control device back to the device PM. If this first status message ACK1_1 is present until the end of the time period TM1, the processor PR does not output the control signal STSP to the alarm output unit WSA2. If, however, no such first status message is present from a control device until the time tmax_I after the end of the time period or the time period TM1, it can be inferred that an alarming at the device PM itself could be necessary. Therefore, the control signal STSP is then outputted by the processor PR to the alarm output unit WSA2.

FIG. 11b further shows an alarming characteristic in a second variant in the case in which a third status message ACK2_1, ACK2_X was sent by the control device to the device PM after the alarming time TAL, and this third status message ACK2_1, ACK2_X indicates in a data element in the above-described manner that a user has acknowledged the alarm at the control device sending the message. Since an alarm output may be suppressed on other control devices or on the control device that has received the acknowledgment, it is, however, possibly necessary to check whether the user, who has acknowledged the alarm and has thus contributed to the suppression of the additional alarm signals, has indeed reached the medical device PM to check the patient's status, the output of an alarm signal is therefore controlled at the device PM itself depending on the second time period or the second time period TM2. If the second time period TM2 ends starting from the time at which the third status message ACK2_1, ACK2_X is received until a time tmax_II, so that no input signal EGS2 of the input unit ES2 of the device PM is present, the control signal STSP is then outputted by the processor PR to the alarm output unit WSA2. It is ensured hereby that the alarm output unit WSA2 will then perform an alarming at least at the medical device PM.

However, if an input of the user on the input unit ES2 of the device PM is detected by the processor PR due to the presence of the input signal EGS2 beginning from the receipt of the third status message ACK2_1, ACK2_X during the time period TM2, no control signal STSP is outputted to the alarm output unit WSA2 after the end of the time period TM2 at the time tmax_II.

The embodiments SG, SG11 of the control device according to the present invention, which were described with reference to FIGS. 2 and 3, may, in turn, also be medical devices SG, SG11 with additional functionalities.

Even though some aspects were described in connection with a device, it is obvious that these aspects also represent a description of the corresponding method, so that a block or a component of a device may also be considered to be a corresponding method step or as a feature of a method step. Analogously to this, aspects that were described in connection with or as a method step also represent a description of a corresponding block/step or detail or feature of a corresponding device, or that the device or the corresponding computer is configured to execute the method step.

The processor provided shall be considered to be at least one computer. The implementation of the at last one computer may also be achieved by a combination of a plurality of computers, preferably by using software in conjunction with hardware. Depending on certain implementation requirements, exemplary embodiments of the present invention may be implemented in hardware and/or in software. The implementation may be achieved with the use of a digital storage medium, for example, a floppy disk, a DVD, a Blu-Ray disk, a CD, a ROM, a PROM, an EPROM, an EEPROM or a FLASH memory, a hard drive or another magnetic or optical memory, on which electrically readable control signals are stored, which can or do interact with a programmable hardware component such that the respective method is executed.

A programmable hardware component may be formed by a processor, a computer processor (CPU=Central Processing Unit), a graphics processor (GPU=Graphics Processing Unit), a computer, a computer system, an application-specific integrated circuit (ASIC=Application-Specific Integrated Circuit), an integrated circuit (IC=Integrated Circuit), a one-chip system (SOC=System on Chip), a programmable logic element or a field-programmable gate array with a microprocessor (FPGA=Field Programmable Gate Array).

The digital storage medium may therefore be machine- or computer-readable. Some exemplary embodiments consequently comprise a data storage medium, which has electronically readable control signals, which are capable of interaction with a programmable computer system or with a programmable hardware component such that one of the methods being described here is executed. An exemplary embodiment is thus a data storage medium (or a digital storage medium or a computer-readable medium), on which the program for executing out the method being described here is recorded.

Exemplary embodiments of the present invention may be implemented, in general, as a program, firmware, computer program or computer program product with a program code or as data, wherein the program code or the data is or are active to the effect that they execute one of the methods when the program runs on a processor or on a programmable hardware component. The program code or the data may also be stored, for example, on a machine-readable medium or data storage medium. The program code or the data may be present, among other things, as source code, machine code or byte code as well as other intermediate codes.

Another exemplary embodiment is further a data stream, a signal sequence or a sequence of signals, which data stream or sequence represents the program for executing one of the methods being described here. The data stream, the signal sequence or the sequence of signals may be configured, for example, to the effect that they can be transferred via a data communication link, for example, over the Internet or another network. Thus, exemplary embodiments also include signal sequences representing data, which are suitable for sending over a network or a data communication link, wherein the data represent the program.

A program according to an exemplary embodiment may implement one of the methods during its execution, for example, by reading memory locations or by writing a datum or a plurality of data in these, whereby switching operations or other processes are possibly elicited in transistor structures, in amplifier structures or in other electrical, optical, magnetic components or in components operating according to another principle of operation. By reading a memory location, values, sensor values or other information can correspondingly be detected, determined or measured by a program. A program can therefore detect, determine or measure variables, values, measured variables and other information by reading one or more memory locations as well as bring about, elicit or execute an action as well as actuate other devices, machines and components by writing in one or more memory locations. While specific embodiments of the invention have been shown and described in detail to illustrate the application of the principles of the invention, it will be understood that the invention may be embodied otherwise without departing from such principles.

APPENDIX

| | |
|---|---|
| Acknowledgment message | ACK, ACK1 1, ACK1 2, ACK2 1, ACK2 X |
| Alarm device | AG |
| List | AL, TL, ML |
| Status element | ALST |
| Request message | ANN |
| Alarm type | ATY |
| Device | AV |
| Bed | B |
| Group message | BC, BC11, BC2, BC3, BC4 |
| Operating state signal | BZ1, BZ2 |
| Data set | DA1, DA2, DA3, DA11, DA22, DA20 |
| Data interface | DAS |
| Signaling interface | DS, SIS |
| Data network interface | DS1, DS2, DSP, DSX, DS |
| Input signal | EGS, EGS2, EGSM |
| Input unit | ES, ES2, ESM |
| Data element | FKT |
| Memory unit | MEM, MEM2, MEMP |
| Mobile unit | MO |
| Rejection message | NACK, NACK1 2 |
| Data network | NW, NW2 |
| Patient | PT |
| Processor | P, P1, PR |
| Medical device | PM, PM1 |
| Sender identity | PMID, PMIDENT |
| Reference value | R |
| Request message | REQ1 |
| Method step | SC1, . . . , SC5, SC11, . . . SC21 |
| Sensor interface | SEC |
| Sensor | SEN |
| Sensor signal | SES |
| Control device | SG, SG11 |
| Network identity | SGID, SGID2 |
| Status information | SIN, SINM |
| Control signal | STS, STS21, STSP |
| Data element | STSGX, EGST, EGSX |
| Timekeeping function | T, TP |
| Time | TA, TB, TC, TAL, tmax I, tmax II |
| Time period | TAR, TBR, TAC, TAD, TM1, TM2 |
| Time value | TV |
| Alarm signal output unit | WSA, WSA1, WSA2, WSAM, WSAX |
| Certificate data | Z1 |

What is claimed is:

1. A control device for controlling an alarm output, the control device being a part of a network unit, the control device comprising:

a data network interface connected to a data network and being configured to receive a group message via the data network, which group message is addressed and sent to a plurality of network units connected to the data network, the plurality of network units to which the group message is addressed and sent including the network unit of which the control device is a part and which group message indicates a sender identity identifying a sender of the group message and which further indicates a presence of an alarm state;

a signaling interface for outputting a control signal, which control signal indicates a request for an output of an acoustic and/or optical alarm signal;

at least one memory unit to provide a first data set, which indicates a list with potential sender identities, as well as further a second data set, which indicates one or more time periods, during which an alarm signal shall be outputted;

an alarm signal output unit for outputting an optical and/or acoustic signal;

an input interface for receiving an input signal, which indicates an acknowledgment of the alarm signal by a user; and at least one processor configured to operate a timekeeping function, with which a start of timekeeping is started on arrival of the group message at the network unit of which the control device is a part, the timekeeping comprising monitoring a time duration from the start of the timekeeping to a current time duration value, and to output the control signal via the signaling interface to the alarm signal output unit as a function of an agreement of the sender identity indicated in the group message with one of the potential sender identities of the first data set as well as further as a function of a comparison of the current time duration value of the timekeeping of the timekeeping function with the one or more time periods data of the second data set, wherein the processor is further configured to suppress the output of the control signal and further to send a status message, which status message indicates the acknowledgment of the alarm signal by the user, to the sender of the group message via the data network interface in the presence of the input signal.

2. A control device in accordance with claim 1, wherein the processor is configured to suppress the output of the control signal no later than when suppression of the output of the control signal is indicated by the one or more time periods of the second data set.

3. A control device in accordance with claim 1, wherein:
the group message has further a data element that indicates a type of an alarm state;
the second data set further indicates an assignment of the time periods to types of alarm states; and
the processor is configured to take into account the type of alarm state indicated in the group message in the course of the comparison.

4. A control device in accordance with claim 1, wherein the processor is further configured:
to check, on the basis of a status information, whether or not the control signal can reach an alarm signal output unit; and
to send a status message, which status message indicates a successful actuation of the alarm signal output unit, to the sender of the group message via the data network interface in case of a positive result of the checking and in case of a beginning of the output of the control signal.

5. A control device in accordance with claim 1, wherein:
the data network interface is further configured to receive a status message via the data network, which status message indicates whether another control device, that is a part of another data network unit of the plurality of data network units to which the group message is addressed and sent, is currently successfully actuating an alarm signal output unit associated therewith; and
the processor is further configured to output the control signal via the signaling interface as a function of a presence of the status message.

6. A control device in accordance with claim 1, wherein:
the data network interface is further configured to receive a status message via the data network, which status message indicates that another control device, that is a part of another data network unit of the plurality of data network units to which the group message is addressed and sent, has detected an acknowledgment of an alarm signal by a user; and
the processor is further configured to suppress the output of the control signal in the presence of the status message.

7. A medical device for analyzing physiological patient data or for monitoring an operating state of at least one device, the medical device comprising:
an alarm signal output unit;
an input unit for manual actuation by a user;
at least one interface for receiving at least one signal, which signal indicates physiological measured values of a patient or at least one operating state of the at least one device;
at least one memory unit for providing a first data set, which first data set indicates at least one physiological or operating state reference value, and a second data set, which second data set indicates a time period, after the end of which time period an output of an alarm shall take place at the alarm signal output unit;
at least one data network interface connected to a data network; and
at least one processor configured to detect the presence of an alarm state by comparing the physiological measured values or the operating state with the physiological or operating state reference value and to output a group message to data network via the at least one data network interface, which group message is addressed to and sent to a plurality of network units connected to the data network, the plurality of network units including a network unit with a control device, configured to generate and send a status message via the data network for receipt by the at least one data network interface, and which group message indicates the presence of the alarm state, if the alarm state is detected and to provide a timekeeping function, with which a start of timekeeping is started upon detecting the alarm state and a time duration is monitored from the start of the timekeeping to a current time duration value, wherein the processor is further configured:
to receive a status message from one of the network units of the data network via the at least one data network interface, which status message indicates an acknowledgment, at said one of the network units, of the alarm state by a user input; and
to output an alarm signal, via the alarm signal output unit, after sending the group message, as a function of a current value of the timekeeping function, as a function of the time period of the second data set, which second data set indicates the time period, as a function of the presence of the status message and as a function of the presence of an input on the input unit.

* * * * *